United States Patent [19]

Rhodes

[11] Patent Number: 5,607,679
[45] Date of Patent: Mar. 4, 1997

[54] LECTINS FOR TREATMENT OF SKIN DISEASES

[75] Inventor: Jonathan M. Rhodes, West Kirby, England

[73] Assignee: British Technology Group Limited, London, England

[21] Appl. No.: 403,700

[22] PCT Filed: Sep. 10, 1993

[86] PCT No.: PCT/GB93/01919

§ 371 Date: Mar. 17, 1995

§ 102(e) Date: Mar. 17, 1995

[87] PCT Pub. No.: WO94/06462

PCT Pub. Date: Mar. 31, 1994

[30] Foreign Application Priority Data

Sep. 19, 1992 [GB] United Kingdom .................. 9219905

[51] Int. Cl.$^6$ ..................................... A61K 7/48
[52] U.S. Cl. ............... 424/401; 424/701; 514/8; 514/863; 514/944
[58] Field of Search .................... 424/401, 701; 514/8, 863, 944

[56] References Cited

U.S. PATENT DOCUMENTS

| | | | |
|---|---|---|---|
| 4,217,341 | 8/1980 | Suddick | 424/48 |
| 4,421,746 | 12/1983 | Kojima et al. | 424/401 |
| 4,440,761 | 4/1984 | Kojima et al. | 424/401 |
| 4,742,046 | 5/1988 | Bliah | 514/8 |

FOREIGN PATENT DOCUMENTS

| | | |
|---|---|---|
| 173092 | 3/1986 | European Pat. Off. . |
| 295955 | 12/1988 | European Pat. Off. . |
| 61-205218A | 9/1986 | Japan . |

*Primary Examiner*—Jyothsna Venkat
*Attorney, Agent, or Firm*—Nixon & Vanderhye

[57] ABSTRACT

Certain lectins, namely those which can bind a sialylated TF antigen, especially the mushroom lectin from *Agaricus bisporus*, are useful in the treatment of skin diseases such as psoriasis and benign keratoses. They may be formulated as, for example, creams, ointments, cosmetic lotions or shampoos.

5 Claims, No Drawings

LECTINS FOR TREATMENT OF SKIN DISEASES

BACKGROUND OF THE INVENTION

1. Field of the Invention

The present invention relates to the use of lectins for the treatment of skin disorders associated with hyperproliferation of keratinocytes or with hyperkeratosis, particularly, but not exclusively, psoriasis and benign keratoses. Lectins are plant or animal proteins or glycoproteins of non-immune origin with specific affinity for carbohydrates.

2. Description of the Related Art

Lectins have been used widely as probes for locating carbohydrate groups in cell membranes, since they have affinities for certain saccharides.

Certain lectins are known to act as mitogens, i.e. stimulators of cell proliferation. For example, peanut agglutinin (PNA) is a mitogen for human colon epithelial cells [S. D. Ryder et al., J. Nat. Cancer Institute 84, 1410–1416 (1992)]. Conconavalin A (Con-A) and phyto-hemagglutinin have a mitogenic effect on haematopoietic cells.

On the other hand, certain lectins have been reported to have an anti-tumour action. See, for example, Japanese Patent Application Publication (Kokai) No. 61-205218, (Ajinomoto K. K.), published in 1986, which mentions the agglutinins of a) *Agaricus bisporus*, b) *Trichosanthes kinlowii*, c) *Rhizobium trifolii*, d) *Salvia horminium*, e) *Maclura pomifera*, f) *Sarothamnus scoparius*, g) *Wistaria floribunda*, h) *Griffonia (Bandeiraea) simplicifolia* and i) *Euonymus europeus*.

SUMMARY OF THE INVENTION

The TF antigen (galactose $\beta$-1,3-N-acetylgalactosamine $\alpha$-) is expressed on normal human keratinocytes. It is the receptor for several lectins including *Arachis hypogaea* (peanut agglutinin), *Amarinthus caudatus* (amarinthin lectin), *Artocarpus integrifolia* (jacalin lectin) and *Agaricus bisporus* lectin. Whereas lectins are well known for their mitogenic properties and whereas previous work by the inventor has shown that peanut agglutinin stimulates proliferation of epithelial cells which express TF antigen, recent studies by the inventor have shown that *Agaricus bisporus* lectin (ABL) has the unusual property of inhibiting proliferation in keratinocytes without causing significant cytotoxicity. Keratinocytes are the predominant cells (>95%) of the epidermis, which is the upper section of the skin tissue. Keratinocytes are continually dividing in the basal layer to produce fresh cells, which migrate towards the skin surface, eventually dying in the upper levels. Hyperproliferation of the epidermis produces excessive scale, comprising dead cells, which is manifested in psoriasis, for example.

Since ABL differs from PNA in its ability to bind sialylated TF antigen, the inventor believes that lectins which bind to sialylated TF antigen inhibit the proliferation of cells.

According to one aspect of the present invention there is provided the use of a lectin, which is capable of binding a sialylated TF antigen, for the treatment of skin disorders caused by or associated with hyperproliferation of keratinocytes or hyperkeratosis. Thus, where patent law permits, the invention includes (1) a method of treating a patient suffering from a skin disorder caused by or associated with hyperproliferation of keratinocytes or hyperkeratosis, especially psoriasis and benign keratoses, which comprises administering to the patient a therapeutically effective amount of a said lectin, and (2) the use of a said lectin in the manufacture of a medicament for the treatment of such a skin disorder.

The medicament may be formulated as a pharmaceutical composition comprising a lectin which is capable of binding sialylated TF antigen and a pharmaceutically acceptable carrier or diluent appropriate to application to the skin. Preferably the composition is a cream, ointment, gel, cosmetic lotion containing a perfume ingredient or a shampoo.

DESCRIPTION OF THE PREFERRED EMBODIMENTS

Jacalin lectin, which comes from the seeds of the jackfruit, *Artocarpus integrifolia*, is another example of a lectin which binds to sialylated TF antigen and its use for the purposes of the invention is also within the invention. Another example of a lectin within the definition is amaranthin (*Amaranthus caudatus*) lectin.

Many lectins, including those specifically referred to above, are commercially available. *Agaricus bisporus* and jacalin lectins, for example, are available from Sigma Chemical Co. Ltd. The preparation of amaranthin has been described by S. J. Rinderle et al., J. Biol. Chem. 264 16123–16131 (1989).

The lectins are preferably formulated for application to the skin in emulsions, solutions or suspensions. Solutions in aqueous or non-toxic organic solvents can be used as skin lotions. Suspensions in water together with surfactants can be used as shampoos for application to the hair, e.g. to treat psoriasis of the scalp. Oil-in-water and water-in-oil emulsions can be formulated for application to irritated skin. Any formulation using ingredients and recipes known in the skin cream, cosmetic lotion or hair shampoo industries, mutatis mutandis, is usable in the present invention.

The concentration of lectin to be applied is preferably within the range 0.01 to 1%, especially 0.05–0.5% and most especially about 0.1% w/w.

The invention is applicable to the treatment of any skin disease caused (at least in part) by excessive growth or proliferation of keratinocytes. For the purposes of the definition of this invention, a disease is considered to be caused at least in part by such proliferation if expert opinion is that it is or may be a contributory factor, so that it would be relevant clinically to treat the disease by reducing or preventing the growth of keratinocytes. The preferred diseases for treatment are those referred to above.

The following Example illustrates the invention

EXAMPLE

The effect of ABL on the proliferation of normal human keratinocytes was studied.

Normal keratinocytes were extracted by trypsinisation from human foreskin, passaged and cultured in CDB153 serum-free medium containing hydrocortisone 50 μmol/l, insulin 5 mg/l, transferrin 5 mg/ml and Epidermal Growth Factor 10 μg/l.

Cell aliquots were cultured for three days at 37° C. in 5% $CO_2$ in the presence of varying concentrations of lectin, each tested in triplicate, then trypsinised, harvested and counted using a Coulter cell counter.

Three separate experiments were carried out. The first two studied two dose ranges of *Agaricus bisporus* lectin: 1–30 μg/ml and 0.1–10 μg/ml respectively. It can be seen from the results in Tables 1 and 2 respectively that there was complete inhibition of proliferation of the keratinocytes at concentrations of lectin of 1 μg/ml or greater. No obvious toxicity (e.g. loss of adherence of cells) was seen at the highest concentration tested (30 μg/ml).

TABLE 1

EFFECT OF MUSHROOM LECTIN (ABL) ON NORMAL HUMAN KERATINOCYTES IN CULTURE (3 DAYS)

| | Cell count ± standard error mean. all × $10^{-5}$ |
|---|---|
| Initial cell count | |
| (all samples) | 0.593 ± .021 |
| 0.1 μg/ml ABL | 2.862 ± 0.048 |
| 0.3 μg/ml ABL | 2.818 ± 0.109 |
| 1 μg/ml ABL | 0.440 ± 0.030 |
| 3 μg/ml ABL | 0.300 ± 0.018 |
| 10 μg/ml ABL | 0.281 ± 0.10 |
| Final cell count | |
| (control) | 3.264 ± 0.035 |

TABLE 2

EFFECT OF MUSHROOM LECTIN (ABL) ON NORMAL HUMAN KERATINOCYTES IN CULTURE (3 DAYS)

| | Cell count ± standard error mean. all × $10^{-5}$ |
|---|---|
| Initial cell count | |
| (all samples) | 2.66 ± 0.008 |
| 1 μg/ml ABL | 3.154 ± 0.115 |
| 3 μg/ml ABL | 2.610 ± 0.090 |
| 10 μg/ml ABL | 2.413 ± 0.049 |
| 30 μg/ml ABL | 2.858 ± 0.028 |
| Final cell count | |
| (control) | 10.514 ± 0.498 |

In the third experiment the effect of different periods of incubation with ABL was investigated. The normal human keratinocytes were incubated with 1 μg/ml. of ABL for 1, 4, 8 and 72 hours, after which the ABL was washed 3× with PBS and replaced by the normal medium. All cells were grown for 72 hours in total and then counted and compared with control cells to which no ABL had been added, incubated for 72 hours. Taking the increase in cell count of the control over the 72 hour period arbitrarily as 100, the corresponding increases in cell count for the samples incubated with ABL were after 1 hour:63 after 4 hours:52 after 8 hours:10 after 72 hours:13

These results indicate that even after washing the cells, the lectin continues to inhibit cell growth.

I claim:

1. A method of treatment of a skin disease caused by or associated with hyperproliferation of keratinocytes, or hyperkeratosis, the method comprising administering to a patient suffering from a said disease an effective amount of a lectin which is capable of binding a sialylated TF antigen.

2. The method of claim 1 wherein the lectin is *Agaricus bisporus* lectin.

3. The method of claim 1 wherein a composition comprising the lectin and a pharmaceutically acceptable carrier or diluent, formulated as a cream, ointment, gel, cosmetic lotion containing a perfume ingredient or a shampoo, is administered to the patient.

4. The method of claim 1 wherein the skin disease is psoriasis.

5. The method of claim 1 wherein the skin disease is a benign keratosis.

* * * * *